US011458127B2

(12) United States Patent
Murtie et al.

(10) Patent No.: US 11,458,127 B2
(45) Date of Patent: Oct. 4, 2022

(54) METHODS OF TREATING BRAIN TUMORS USING COMBINATION THERAPY

(71) Applicant: SERVIER PHARMACEUTICALS LLC, Boston, MA (US)

(72) Inventors: Joshua Murtie, Winchester, MA (US); Nelamangala Nagaraja, Lexington, MA (US); Brandon Nicolay, Manchester, MA (US); David Schenkein, Boston, MA (US); Katharine Yen, Wellesley, MA (US)

(73) Assignee: AGIOS PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/006,234

(22) Filed: Jun. 12, 2018

(65) Prior Publication Data
US 2018/0353491 A1 Dec. 13, 2018

Related U.S. Application Data

(60) Provisional application No. 62/518,562, filed on Jun. 12, 2017.

(51) Int. Cl.
*A61K 31/444* (2006.01)
*A61P 35/00* (2006.01)
*A61K 31/44* (2006.01)
*A61K 31/495* (2006.01)
*A61K 31/7068* (2006.01)
*C07K 16/22* (2006.01)
*A61K 41/00* (2020.01)
*A61K 45/06* (2006.01)

(52) U.S. Cl.
CPC ............ *A61K 31/444* (2013.01); *A61K 31/44* (2013.01); *A61K 31/495* (2013.01); *A61K 31/7068* (2013.01); *A61P 35/00* (2018.01); *C07K 16/22* (2013.01); *A61K 41/0038* (2013.01); *A61K 45/06* (2013.01)

(58) Field of Classification Search
CPC ....... A61P 35/00; A61K 31/444; A61K 31/44; A61K 41/0038
USPC ........................................................ 514/333
See application file for complete search history.

(56) References Cited

U.S. PATENT DOCUMENTS 9,474,779 B2 * 10/2016 Lemieux .............. C07D 205/08
9,579,324 B2 2/2017 Konteatis
9,850,277 B2 * 12/2017 Popovici-Muller .........................
 C07D 205/08
2013/0190249 A1 * 7/2013 Lemieux .............. C07D 401/14
 514/19.3
2015/0018328 A1 1/2015 Konteatis et al.

FOREIGN PATENT DOCUMENTS

| JP | 9-509966 | 7/1997 | | |
|---|---|---|---|---|
| JP | H10-45589 A | 2/1998 | | |
| JP | 2014-523421 A | 9/2014 | | |
| JP | 2015-509098 A | 3/2015 | | |
| JP | 2015-525798 A | 9/2015 | | |
| JP | 2016-525130 A | 8/2016 | | |
| JP | 2016/526561 A | 9/2016 | | |
| WO | WO 2015/003640 A1 | 1/2015 | | |
| WO | WO 2015/010297 | 1/2015 | | |
| WO | WO-2015003640 A1 * | 1/2015 | ........... | C07D 401/14 |
| WO | WO-2015121209 A1 * | 8/2015 | ........... | C07D 235/30 |
| WO | 2017/004532 A1 | 1/2017 | | |
| WO | 2017066571 A1 | 4/2017 | | |
| WO | WO 2017/066566 | 4/2017 | | |
| WO | 2017/059224 A3 | 5/2017 | | |

OTHER PUBLICATIONS

Sulkowski et al, Sci. Translational Medicine. (Year: 2017).*
External beam radiation dose escalation for high grade glioma . Khan L et al (Year: 2016).*
Hui Yang et al IDH1 and IDH2 mutations in tumorigenesis : mechanistic insights and clinical perspectives (Year: 2012).*
Young-Sam Keum et al Isocitrate dehydrogenase mutationsmew opportunities for translational research. (Year: 2015).*
Kourosh Jafari-Khouzani et al. Volumetric relationship between 2-hydroxyglutarate and FLAIR hyperintensity has potential implications for radiotherapy planning of mutant IDH glioma patients. (Year: 2016).*
Mizoe jun-Etsu et al. Malignant Gliomas ; combined X-ray radiotherapy, chemotherapy, and carbon ion radiotherapy. (Year: 2007).*
Hai Yan et al IDH1 and IDH2 mutations in Gliomas (Year: 2009).*
Molenaar et al Wild-type and mutated IDH1/2 enzymes and therapy responses. (Year: 2018).*
L. Dang et al . IDH mutations in cancer and progress towards development of targeted therapeutics (Year: 2016).*
"The National Comprehensive Cancer Network Guidelines Version 1.2016 Updates Central Nervous System Cancers," Jul. 25, 2016, pp. 1-123.
"The National Comprehensive Cancer Network Guidelines Version 1.2016 Sub-Committees Central Nervous System Cancers—NCCN Evidence Blocks," Aug. 25, 2016, pp. 1-124.
Berge, S.M., et al., "Pharmaceutical salts," J. Pharmaceutical Sciences, 66, 1977, pp. 1-19.
Dang, L. et al., "Cancer-associated IDH1 mutations produce 2-hydroxyglutarate," Nature 462, 2009, pp. 739-744.
Geisbrecht, Brian V., et al., "The Human PICD Gene Encodes a Cytoplasmic and Peroxisomal NADP+-dependent Isocitrate Dehydrogenase," J. Biol. Chem. 274, 1999, pp. 30527-30533.
Gerhard, Daniela S. et al., The MBC Project Team "The Status, Quality, and Expansion of the NIH Full-Length cDNA Project: The Mammalian Gene Collection (MGC)," Genome Res. 14, 2004, pp. 2121-2127.

(Continued)

Primary Examiner — Jeffrey S Lundgren
Assistant Examiner — Michael J Schmitt
(74) Attorney, Agent, or Firm — Goodwin Procter LLP

(57) ABSTRACT

Provided are methods of treating a brain tumor in a patient in need thereof comprising administering to the patient a compound described herein and radiation therapy and/or one or more additional therapeutic agents.

13 Claims, 1 Drawing Sheet

(56) References Cited

OTHER PUBLICATIONS

Nekrutenko, Anton, et al., "Cytosolic isocitrate dehydrogenase in humans, mice, and voles and phylogenetic analysis of the enzyme family," Mol. Biol. Evol. 15, 1998, pp. 1674-1684.
Nicolay et al., Abstract "Combined Use of the pan-IDH Mutant Inhibitor AG-881 with Radiation Therapy Shows Added Benefit in an Orthotopic IDH1 Mutant Glioma Model in Vivo," Neuro-Oncology, Nov. 6, 2017, 15(suppl_6): p. vi79.
Nicolay et al., Abstract "The IDH1 mutant inhibitor AG-120 shows strong inhibition of 2-HG production in an orthotopic IDH1 mutant glioma model in vivo," Neuro-Oncology, Nov. 2017, vi86.
Shirley, V.S., et al. "Table of Nuclides", Isotopes Project, Nuclear Science Division, Lawrence Berkeley Laboratory, Jan. 1980.
Sjoblom et al., "The Consensus Coding Sequences of Human Breast and Colorectal Cancers," Science 314, 2006, pp. 268-274.
Wiemann, Stefan, et al., "Toward a Catalog of Human Genes and Proteins: Sequencing and Analysis of 500 Novel Complete Protein Coding Human cDNAs," Genome Res. 11, 2001, pp. 422-435.
Office Action dated Feb. 11, 2019, in U.S. Appl. No. 16/006,202, filed Jun. 12, 2018.
Mizoe, Jun-Etsu et al., "Phase I/II clinical trial of carbon ion radiotherapy for malignant gliomas: combined X-ray radiotherapy, chemotherapy, and carbon ion radiotherapy.", Int J Radiat Oncol Biol Phys. Oct. 1, 2007, p. 390-396, vol. 69, No. 2.
International Search Report dated Oct. 8, 2018, prepared in International Application No. PCT/US2018/037066.
Written Opinion prepared in International Application No. PCT/US2018/037066.
Final Office Action dated Jul. 26, 2019, in U.S. Appl. No. 16/006,202, filed Jun. 12, 2018.
Tran, et al: Increased sensitivity to radiochemotherapy in IDH1 mutant glioblastoma as demonstrated by serial quantitative MR volumetry; Neuro-Oncology 16(3), 414-420, 2014.
Barani et al, Radiation Therapy of Glioblastoma, Raizer and Parsa, eds., Current Understanding and Treatment f Gliomas, Cancer Treatment Research, 164, pp. 49-73, 2015.
Sonoda et al. 2-hydroxyglutarate accumulation caused by IDH mutation is involved in the formation of malignant gliomas, Expert Review of Neurotherapeutics, 10:4, 487-489, 2010.
Molenaar et al., "Radioprotection of IDH1-Mutated Cancer Cells by the IDH1-Mutant Inhibitor AGI-5198," Cancer Res; 75(22); Nov. 15, 2015, pp. 4790-4802.
Kristen A Batich and John H. Sampson, MD, PhD, "Standard of care and future pharmacological treatment options for malignant glioma; an urgent need for screening and identification of novel tumor-specific antigens," *Expert Opin Pharmacother* 15(14):—Author manuscript; Oct. 2014, pp. 2047-2061.
Rohle et al., "An Inhibitor of Mutant IDH1 Delays Growth and Promotes Differentiation of Glioma Cells," *Science* 340 (6132)—Author Manuscript, May 2013, pp. 626-630.
TS Jones and EC Holland, "Standard of Care Therapy for Malignant Glioma and Its Effect on Tumor and Stromal Cells," *Oncogene* (2012) 31, pp. 1995-2006.
Sulkowski et al., "2-Hydroxyglutarate produced by neomorphic IDH mutations suppresses homologous recombination and induces PARP inhibitor sensitivity," *Sci. Transl. Med.* 9, Feb. 1, 2017; pp. 1-15.
TEMODAR—Highlights of Prescribing Information, pp. 1-17.
Jiao Chen, Jie Yang and Peng Cao, "The Evolving Landscape in the Development of Isocitrate Dehydrogenase Mutant Inhibitors," *Mini-Reviews in Medicinal Chemistry*, vol. 16, No. 16, pp. 1344-1358.
Popovici-Muller, Janeta, "Discovery of the first potent in hibitors of Mutant IDH1 that lower tumor 2-hg in vivo" ACS Medicinal Chemistry Letters, 2012, p. 850-855, vol. 3.
Annals of Oncology, 2016, vol. 27, pp. 599-608.
History of Changes for Study: NCT03173248 "Study of AG-120 (Ivosidenib) vs. Placebo in Combination With Azacitidine in Patients With Previously Untreated Acute Myeloid Leukemia With an IDH1 Mutation (AGILE)" [online], May 30, 2017, [retrieved on Mar. 17, 2020], Retrieved from the Internet: URL: https://clinicaltrials.gov/ct2/history/NCT0317248?A=1&B=1&C=merged#StudyPageTop <https://protect-us.mimecast.com/s/amwrCG69wxcPxK9BcQWhhl?domain=clinicaltrials.gov>.
WHO Drug Information, 2015, vol. 29, No. 4, pp. 533-534.
Jpn J Neurosurg, 2015, vol. 24, No. 6, pp. 378-385.
Non profit organization, Japanese Society for Palliative Medicine, gantotsu no yakubutsuryoho ni kansuru gaidorain (guidelines of drug therapy for cancer pain) (2010) [online], 2010, [retrieved on Mar. 17, 2022], Retrieved from the Internet: <URL:https://www.jspm.ne.jp/guidelines/pain/2010/chapter03/03_00.php <https://protect-US.mimecast.eom/s/>9pLCJ6PEAc2G3oBhv3b19?domain=jspm.ne.jp>>, the section of "Chapter 3 Suisho (recommendation) ?suisho no gaiyo (summary of recommendation) OVERVIEW".
Jpn J Neurosurg, 2012, vol. 21, No. 3, pp. 216-223.
U.S. Appl. No. 13/810,410, filed Mar. 28, 2013, Janeta Popovici-Muller et al.
U.S. Appl. No. 15/064,874, filed Mar. 9, 2016, Janeta Popovici-Muller et al.
U.S. Appl. No. 13/745,005, filed Jan. 18, 2013, Rene M. Lemieux et al.
U.S. Appl. No. 14/988,661, filed Jan. 5, 2016, Rene M. Lemieux et al.
U.S. Appl. No. 15/279,146, filed Sep. 28, 2016, Janeta Popovici-Muller et al.
U.S. Appl. No. 15/809,325, filed Nov. 10, 2017, Janeta Popovici-Muller et al.
U.S. Appl. No. 16/427,691, filed May 31, 2019, Janeta Popovici-Muller et al.
U.S. Appl. No. 16/893,750, filed Jun. 5, 2020, Janeta Popovici-Muller et al.
U.S. Appl. No. 14/373,154, filed Jul. 18, 2014, Janeta Popovici-Muller et al.
U.S. Appl. No. 15/196,842, filed Jun. 19, 2016, Janeta Popovici-Muller et al.
U.S. Appl. No. 14/341,426, filed Jul. 25, 2014, Rene M. Lemieux et al.
U.S. Appl. No. 15/347,407, filed No. 9, 2016, Rene M. Lemieux et al.
U.S. Appl. No. 15/915,213, filed Mar. 8, 2018, Rene M. Lemieux et al.
U.S. Appl. No. 16/871,777, filed May 11, 2020, Rene M. Lemieux et al.
U.S. Appl. No. 15/125,884, filed Sep. 13, 2016, Chong-Hui Gu.
U.S. Appl. No. 15/125,880, filed Sep. 13, 2016, Chong-Hui Gu.
U.S. Appl. No. 15/949,750, filed Apr. 10, 2018, Chong-Hui Gu.
U.S. Appl. No. 16/460,111, filed Jul. 2, 2019, Chong-Hui Gu.
U.S. Appl. No. 17/013,083, filed Sep. 4, 2020, Chong-Hui Gu.
U.S. Appl. No. 15/767,813, filed Apr. 12, 2018, Samuel V. Agresta et al.
U.S. Appl. No. 15/767,822, filed Apr. 12, 2018, Samuel V. Agresta et al.
U.S. Appl. No. 16/846,976, filed Apr. 13, 2020, Samuel V. Agresta et al.
U.S. Appl. No. 15/781,019, filed Jun. 1, 2018, Bin Wu et al.
U.S. Appl. No. 17/318,606, filed May 12, 2021, Bin Wu et al.
U.S. Appl. No. 16/079,802, filed Aug. 24, 2018, Sung Eun Choe et al.
U.S. Appl. No. 16/869,238, filed May 7, 2020, Sung Eun Choe et al.
U.S. Appl. No. 16/434,307, filed Jun. 7, 2019, Samuel V. Agresta.
U.S. Appl. No. 17/203,433, filed Mar. 16, 2021, Samuel V. Agresta.
U.S. Appl. No. 17/634,524, filed Feb. 10, 2022, Jacob Paul Sizemore et al.
U.S. Appl. No. 17/258,102, filed Jan. 5, 2021, Chong-Hui Gu et al.
U.S. Appl. No. 16/619,526, filed Dec. 5, 2019, Joshua Murtie et al.
U.S. Appl. No. 16/006,202, filed Jun. 12, 2018, Joshua Murtie et al.
U.S. Appl. No. 17/001,741, filed Aug. 25, 2020, Joshua Murtie et al.

* cited by examiner

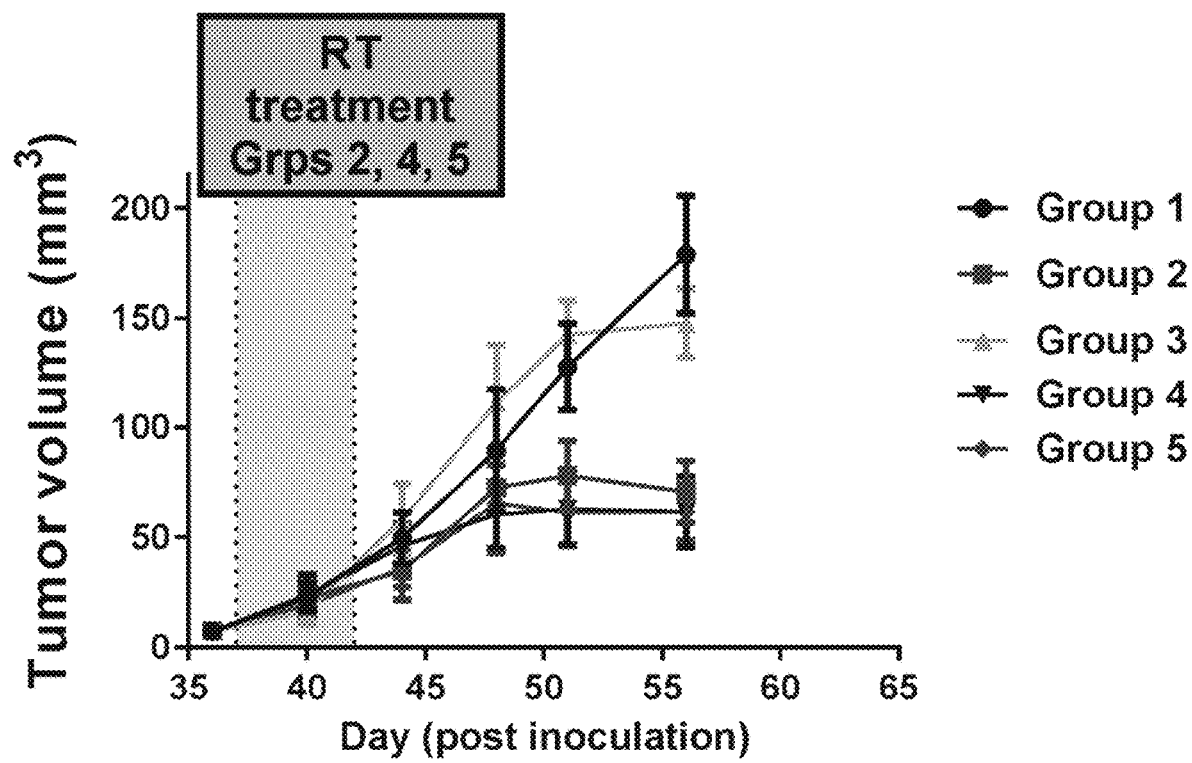

METHODS OF TREATING BRAIN TUMORS USING COMBINATION THERAPY

BACKGROUND

Isocitrate dehydrogenases (IDHs) catalyze the oxidative decarboxylation of isocitrate to 2-oxoglutarate (i.e., α-ketoglutarate). These enzymes belong to two distinct subclasses, one of which utilizes NAD(+) as the electron acceptor and the other NADP(+). Five isocitrate dehydrogenases have been reported: three NAD(+)-dependent isocitrate dehydrogenases, which localize to the mitochondrial matrix, and two NADP(+)-dependent isocitrate dehydrogenases, one of which is mitochondrial and the other predominantly cytosolic. Each NADP(+)-dependent isozyme is a homodimer.

IDH1 (isocitrate dehydrogenase 1 (NADP+), cytosolic) is also known as IDH; IDP; IDCD; IDPC or PICD. The protein encoded by this gene is the NADP(+)-dependent isocitrate dehydrogenase found in the cytoplasm and peroxisomes. It contains the PTS-1 peroxisomal targeting signal sequence. The presence of this enzyme in peroxisomes suggests roles in the regeneration of NADPH for intraperoxisomal reductions, such as the conversion of 2, 4-dienoyl-CoAs to 3-enoyl-CoAs, as well as in peroxisomal reactions that consume 2-oxoglutarate, namely the alpha-hydroxylation of phytanic acid. The cytoplasmic enzyme serves a significant role in cytoplasmic NADPH production.

The human IDH1 gene encodes a protein of 414 amino acids. The nucleotide and amino acid sequences for human IDH1 can be found as GenBank entries NM_005896.2 and NP_005887.2 respectively. The nucleotide and amino acid sequences for IDH1 are also described in, e.g., Nekrutenko et al., Mol. Biol. Evol. 15:1674-1684(1998); Geisbrecht et al., J. Biol. Chem. 274:30527-30533(1999); Wiemann et al., Genome Res. 11:422-435(2001); The MGC Project Team, Genome Res. 14:2121-2127(2004); Lubec et al., Submitted (December-2008) to UniProtKB; Kullmann et al., Submitted (June 1996) to the EMBL/GenBank/DDBJ databases; and Sjoeblom et al., Science 314:268-274(2006).

Non-mutant, e.g., wild type, IDH1 catalyzes the oxidative decarboxylation of isocitrate to α-ketoglutarate.

It has been discovered that mutations of IDH1 present in certain cancer cells result in a new ability of the enzyme to catalyze the NAPH-dependent reduction of α-ketoglutarate to R(−)-2-hydroxyglutarate (2HG). The production of 2HG is believed to contribute to the formation and progression of cancer (Dang, L et al., Nature 2009, 462:739-44).

IDH2 (isocitrate dehydrogenase 2 (NADP+), mitochondrial) is also known as IDH; IDP; IDHM; IDPM; ICD-M; or mNADP-IDH. The protein encoded by this gene is the NADP(+)-dependent isocitrate dehydrogenase found in the mitochondria. It plays a role in intermediary metabolism and energy production. This protein may tightly associate or interact with the pyruvate dehydrogenase complex. Human IDH2 gene encodes a protein of 452 amino acids. The nucleotide and amino acid sequences for IDH2 can be found as GenBank entries NM_002168.2 and NP_002159.2 respectively. The nucleotide and amino acid sequence for human IDH2 are also described in, e.g., Huh et al., Submitted (November-1992) to the EMBL/GenBank/DDBJ databases; and The MGC Project Team, Genome Res. 14:2121-2127(2004).

Non-mutant, e.g., wild type, IDH2 catalyzes the oxidative decarboxylation of isocitrate to α-ketoglutarate (α-KG).

It has been discovered that mutations of IDH2 present in certain cancer cells result in a new ability of the enzyme to catalyze the NAPH-dependent reduction of α-ketoglutarate to R(−)-2-hydroxyglutarate (2HG). 2HG is not formed by wild-type IDH2. The production of 2HG is believed to contribute to the formation and progression of cancer (Dang, L et al, Nature 2009, 462:739-44).

Mutations in IDH1 or IDH2 occur in over 70% of diffuse low grade glioma (LGG) tumors. IDH mutations result in accumulation of 2-HG, which is believed to facilitate tumorigenesis through DNA hypermethylation, increased repressive histone methylation, and inhibition of differentiation processes. Studies performed with a tool compound known as AGI-5198, which has been shown to inhibit mutant IDH1 (mIDH1), but not mutant IDH2 (mIDH2), have demonstrated that inhibition of mIDH1 proteins can repress growth of mIDH1-driven gliomas in some model systems (D. Rohle et al. Science 340:626-630 (2013)). However, recent in vitro studies in mIDH1 glioma models showed that mIDH1 cells treated with AGI-5198 were desensitized to radiation therapy, and the authors of these studies suggested that administration of mIDH1 inhibitors during radiation therapy may result in an unfavorable clinical outcome (R. J. Molenaar et al., Cancer Research 75:4790-4802 (2015)).

U.S. Publication No. 2013/0190249 A1 discloses a compound described by the chemical name (S)—N—((S)-1-(2-Chlorophenyl)-2-(3,3-difluorocyclobutylamino)-2-oxo-ethyl)-1-(4-cyanopyridin-2-yl)-N-(5-fluoropyridin-3-yl)-5-oxopyrrolidine-2-carboxamide, which has been shown to act as an inhibitor of mutant IDH1 proteins in biochemical and cellular assays.

SUMMARY OF INVENTION

The invention provides methods of treating a brain tumor in a patient in need thereof comprising administering to the patient a compound described herein and radiation therapy and/or one or more additional therapeutic agents.

In one aspect, the invention provides a method for treating a brain tumor in a patient in need thereof comprising administering to the patient (a) a compound of formula (I)

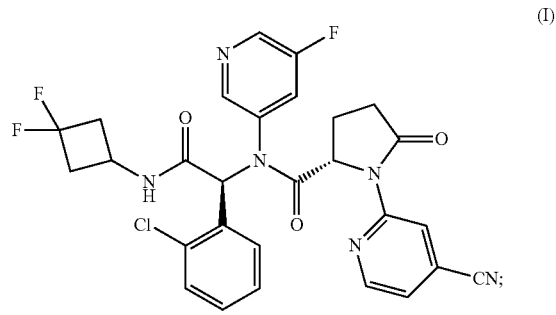 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt thereof; and (b) radiation therapy; in amounts effective for treating the brain tumor.

In another aspect, the invention provides a method for treating a brain tumor in a patient in need thereof comprising administering to the patient (a) a compound of formula (I)

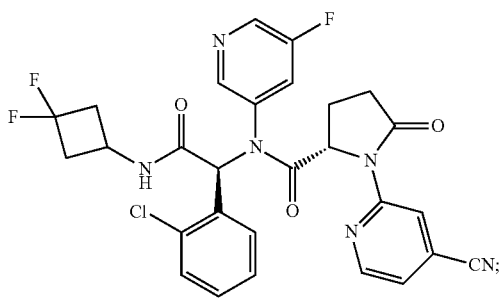

(I)

or a pharmaceutically acceptable salt thereof; and (b) one or more additional therapeutic agents; in amounts effective for treating the brain tumor.

In another aspect, the invention provides a method for treating a brain tumor in a patient in need thereof comprising administering to the patient (a) a compound of formula (I)

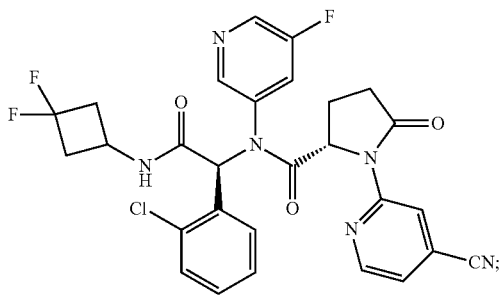

(I)

or a pharmaceutically acceptable salt thereof; (b) radiation therapy; and (c) one or more additional therapeutic agents; in amounts effective for treating the brain tumor.

BRIEF DESCRIPTION OF THE DRAWINGS

FIG. 1 is a graph of median tumor volume versus time in an IHD1m glioma mouse model during treatment with vehicle, radiation therapy, Ivosidenib, and combinations of radiation therapy and Ivosidenib.

DETAILED DESCRIPTION OF THE INVENTION

In one aspect, the invention provides a method for treating a brain tumor in a patient in need thereof comprising administering to the patient (a) a compound of formula (I)

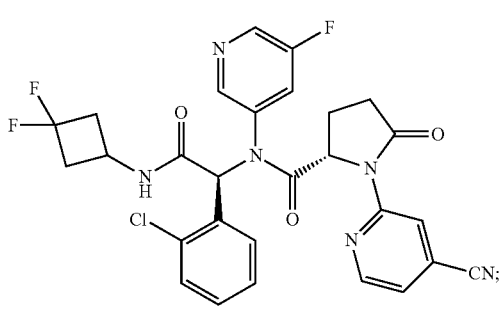

(I)

or a pharmaceutically acceptable salt thereof; and (b) radiation therapy; in amounts effective for treating the brain tumor.

In some embodiments, the compound of formula (I) is administered in non-salt (i.e., free base) form.

The radiation therapy may be administered concurrently with or sequentially with (prior to or following) the administration of the compound of formula (I), or a pharmaceutically acceptable salt thereof. In some embodiments, the compound of formula (I), or a pharmaceutically acceptable salt thereof, and the radiation therapy are administered concurrently. In other embodiments, the compound of formula (I), or a pharmaceutically acceptable salt thereof, and the radiation therapy are administered sequentially. For example, in some embodiments, the compound of formula (I), or a pharmaceutically acceptable salt thereof, is administered prior to the radiation therapy. In other embodiments, the radiation therapy is administered prior to the compound of formula (I), or a pharmaceutically acceptable salt thereof.

In another aspect, the invention provides a method for treating a brain tumor in a patient in need thereof comprising administering to the patient (a) a compound of formula (I)

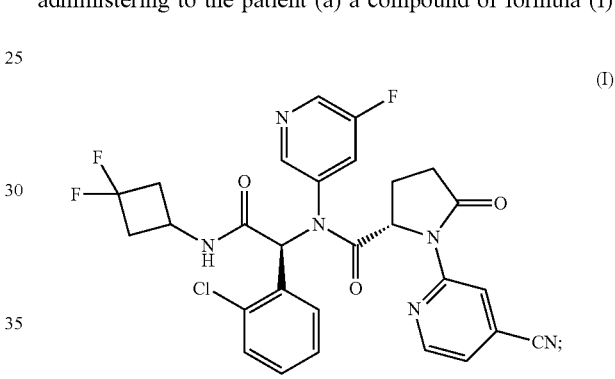

(I)

or a pharmaceutically acceptable salt thereof; and (b) one or more additional therapeutic agents; in amounts effective for treating the brain tumor.

In some embodiments, the compound of formula (I) is administered in non-salt (i.e., free base) form.

The one or more additional therapeutic agents may be administered together with the compound of formula (I), or a pharmaceutically acceptable salt thereof, in a single dosage form (e.g., pharmaceutical composition) or as a separate dosage form. If administered as a separate dosage form, the one or more additional therapeutic agents may be administered concurrently with or sequentially with (prior to or following) the administration of the compound of formula (I), or a pharmaceutically acceptable salt thereof. In some embodiments, the compound of formula (I), or a pharmaceutically acceptable salt thereof, and the one or more additional therapeutic agents are administered concurrently. In other embodiments, the compound of formula (I), or a pharmaceutically acceptable salt thereof, and the one or more additional therapeutic agents are administered sequentially. For example, in some embodiments, the compound of formula (I), or a pharmaceutically acceptable salt thereof, is administered prior to the one or more additional therapeutic agents. In other embodiments, the one or more additional therapeutic agents are administered prior to the compound of formula (I), or a pharmaceutically acceptable salt thereof.

In another aspect, the invention provides a method for treating a brain tumor in a patient in need thereof comprising administering to the patient (a) a compound of formula (I)

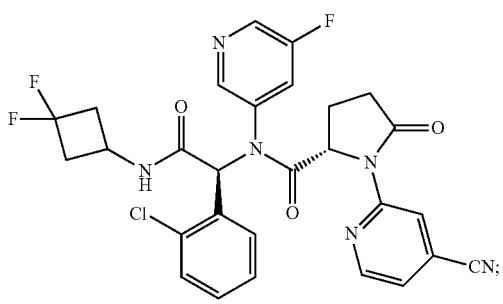

(I)

or a pharmaceutically acceptable salt thereof; (b) radiation therapy; and (c) one or more additional therapeutic agents; in amounts effective for treating the brain tumor.

In some embodiments, the compound of formula (I) is administered in non-salt (i.e., free base) form.

The one or more additional therapeutic agents may be administered together with the compound of formula (I), or a pharmaceutically acceptable salt thereof, in a single dosage form (e.g., pharmaceutical composition) or as a separate dosage form. If the compound of formula (I), or a pharmaceutically acceptable salt thereof, and the one or more additional therapeutic agents are administered in a single dosage form, the single dosage form may be administered concurrently with or sequentially with (prior to or following) the administration of the radiation therapy.

If the compound of formula (I), or a pharmaceutically acceptable salt thereof, and the one or more additional therapeutic agents are administered as separate dosage forms, the compound of formula (I), or a pharmaceutically acceptable salt thereof, one or more additional therapeutic agents, and radiation therapy may be administered concurrently with one another or sequentially in any order.

In another aspect, the invention provides a method for treating a brain tumor in a patient in need thereof comprising administering to the patient (a) a compound of formula (I)

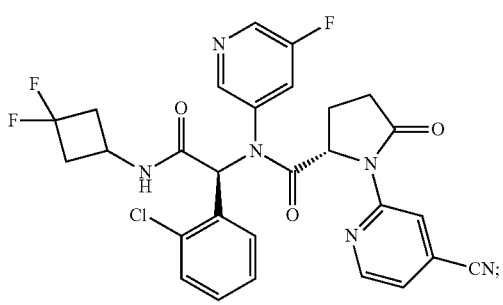

(I)

or a pharmaceutically acceptable salt thereof; and (b) a DNA-reactive agent; in amounts effective for treating the brain tumor.

In some embodiments, the compound of formula (I) is administered in non-salt (i.e., free base) form.

The DNA-reactive agent may be administered together with the compound of formula (I), or a pharmaceutically acceptable salt thereof, in a single dosage form (e.g., pharmaceutical composition) or as a separate dosage form. If administered as a separate dosage form, the DNA-reactive agent may be administered concurrently with or sequentially with (prior to or following) the administration of the compound of formula (I), or a pharmaceutically acceptable salt thereof. In some embodiments, the compound of formula (I), or a pharmaceutically acceptable salt thereof, and the DNA-reactive agent are administered concurrently. In other embodiments, the compound of formula (I), or a pharmaceutically acceptable salt thereof, and the DNA-reactive agent are administered sequentially. For example, in some embodiments, the compound of formula (I), or a pharmaceutically acceptable salt thereof, is administered prior to the DNA-reactive agent. In other embodiments, the DNA-reactive agent is administered prior to the compound of formula (I), or a pharmaceutically acceptable salt thereof.

In another aspect, the invention provides a method for treating a brain tumor in a patient in need thereof comprising administering to the patient (a) a compound of formula (I)

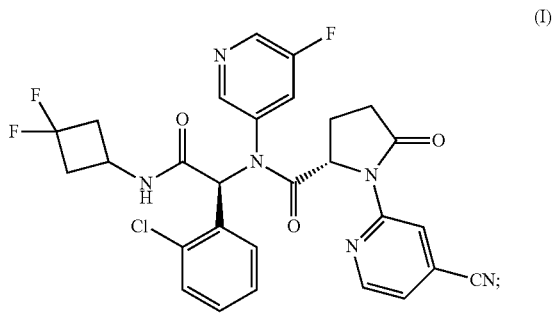 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

(I)

or a pharmaceutically acceptable salt thereof; (b) radiation therapy; and (c) a DNA-reactive agent; in amounts effective for treating the brain tumor.

In some embodiments, the compound of formula (I) is administered in non-salt (i.e., free base) form.

The DNA-reactive agent may be administered together with the compound of formula (I), or a pharmaceutically acceptable salt thereof, in a single dosage form (e.g., pharmaceutical composition) or as a separate dosage form. If the compound of formula (I), or a pharmaceutically acceptable salt thereof, and the DNA-reactive agent are administered in a single dosage form, the single dosage form may be administered concurrently with or sequentially with (prior to or following) the administration of the radiation therapy.

If the compound of formula (I), or a pharmaceutically acceptable salt thereof, and the DNA-reactive agent are administered as separate dosage forms, the compound of formula (I), or a pharmaceutically acceptable salt thereof, DNA-reactive agent, and radiation therapy may be administered concurrently with one another or sequentially in any order.

In another aspect, the invention provides a compound of formula (I), or a pharmaceutically acceptable salt thereof, for use in any of the methods described herein.

In another aspect, the invention provides the use of a compound of formula (I), or a pharmaceutically acceptable salt thereof, for the manufacture of a medicament for use in any of the methods described herein.

As used herein, the phrase "amounts effective" refers to the amounts of the compound of formula (I), or a pharmaceutically acceptable salt thereof, and radiation therapy and/or one or more additional therapeutic agents (e.g., DNA-reactive agent) that are sufficient, when administered in combination, to achieve a therapeutic benefit for treating a brain tumor in the methods described herein. The amounts effective in the methods described herein may or may not be the same as the amounts that are effective when the compound of formula (I), or a pharmaceutically acceptable salt thereof, radiation therapy, or one or more additional therapeutic agents (e.g., DNA-reactive agent) is administered as a monotherapy. In some embodiments, the amount of the compound of formula (I), or a pharmaceutically acceptable salt thereof, that is effective in the methods described herein is the same as, less than, or more than the amount of the compound of formula (I), or a pharmaceutically acceptable salt thereof, that is effective when the compound of formula (I), or a pharmaceutically acceptable salt thereof, is administered as a monotherapy. In some embodiments, the amount of radiation therapy that is effective in the methods described herein is the same as, less than, or more than the amount of radiation therapy that is effective when radiation therapy is administered as a monotherapy. In some embodiments, the amount of the one or more additional therapeutic agents (e.g., DNA-reactive agent) that is effective in the methods described herein is the same as, less than, or more than the amount of the one or more additional therapeutic agents (e.g., DNA-reactive agent) that is effective when the one or more additional therapeutic agents (e.g., DNA-reactive agent) is administered as a monotherapy.

As used herein, the term "treating," when referring to a brain tumor, means having a therapeutic effect on, alleviating one or more symptoms of, altering the progression of, eradicating, reducing the size of, slowing or inhibiting the growth of, delaying or minimizing one or more symptoms associated with, reducing the malignancy of, or inducing stasis of the brain tumor, or alleviating or minimizing one or more side effects associated with another therapy administered or applied to treat the brain tumor. In some embodiments, "treating" comprises reducing the size of or slowing or inhibiting the growth of the brain tumor. In some embodiments, "treating" comprises reducing the size of or slowing or inhibiting the growth of the brain tumor for a period of time, followed by stasis of the brain tumor. In some embodiments, "treating" comprises having a therapeutic effect on, alleviating the symptoms of, altering the progression of, or inducing stasis of the brain tumor without affecting the size of the brain tumor. In some embodiments, "treating" comprises reducing the number or percentage of malignant cells in a brain tumor.

In one embodiment, the methods provided herein provide a complete response, partial response or stable disease in patients having glioma.

In one embodiment, the methods provided herein increase the overall survival of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the complete remission rate of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the objective response rate of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the time to progression of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the relapse free survival of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the progression free survival of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the event-free survival of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the duration of remission of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the duration or response of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the time to remission/response of patients having glioma when treated with an effective amount of the compound of formula (I), or a pharmaceutically acceptable salt thereof, as compared to patients that are not treated with the compound of formula (I), or a pharmaceutically acceptable salt thereof.

In one embodiment, the methods provided herein increase the overall survival of patients having glioma as compared to patients that are treated with the compound of formula (I), or a pharmaceutically acceptable salt thereof, radiation therapy, or one or more additional therapeutic agents individually.

In one embodiment, the methods provided herein increase the complete remission rate of patients having glioma as compared to patients that are treated with the compound of formula (I), or a pharmaceutically acceptable salt thereof, radiation therapy, or one or more additional therapeutic agents individually.

In one embodiment, the methods provided herein increase the objective response rate of patients having glioma as compared to patients that are treated with the compound of formula (I), or a pharmaceutically acceptable salt thereof, radiation therapy, or one or more additional therapeutic agents individually.

In one embodiment, the methods provided herein increase the time to progression of patients having glioma as compared to patients that are treated with the compound of formula (I), or a pharmaceutically acceptable salt thereof, radiation therapy, or one or more additional therapeutic agents individually.

In one embodiment, the methods provided herein increase the relapse free survival of patients having glioma as compared to patients that are treated with the compound of formula (I), or a pharmaceutically acceptable salt thereof, radiation therapy, or one or more additional therapeutic agents individually.

In one embodiment, the methods provided herein increase the progression free survival of patients having glioma as compared to patients that are treated with the compound of formula (I), or a pharmaceutically acceptable salt thereof, radiation therapy, or one or more additional therapeutic agents individually.

In one embodiment, the methods provided herein increase the event-free survival of patients having glioma as compared to patients that are treated with the compound of formula (I), or a pharmaceutically acceptable salt thereof, radiation therapy, or one or more additional therapeutic agents individually.

In one embodiment, the methods provided herein increase the duration of remission of patients having glioma as compared to patients that are treated with the compound of formula (I), or a pharmaceutically acceptable salt thereof, radiation therapy, or one or more additional therapeutic agents individually.

In one embodiment, the methods provided herein increase the duration or response of patients having glioma as compared to patients that are treated with the compound of formula (I), or a pharmaceutically acceptable salt thereof, radiation therapy, or one or more additional therapeutic agents individually.

In one embodiment, the methods provided herein increase the time to remission/response of patients having glioma as compared to patients that are treated with the compound of formula (I), or a pharmaceutically acceptable salt thereof, radiation therapy, or one or more additional therapeutic agents individually.

As used herein, the term "complete response" refers to the disappearance of all signs of cancer in response to treatment. This does not always mean the cancer has been cured. The term is also interchangeable in the art with "complete remission."

As used herein, the term "partial response" refers to a decrease in the size of a tumor, or in the extent of cancer in the body, in response to treatment. The term is also interchangeable in the art with "partial remission."

As used herein, the term "stable disease" refers to cancer that is neither increasing nor decreasing in extent or severity.

As used herein, the term "overall survival" (OS) means the time from randomization in a clinical trial until death from any cause.

As used herein, the term "complete remission rate" refers to complete disappearance of all such manifestations of disease.

As used herein, the term "objective response rate" (ORR) refers to the proportion of patients with tumor size reduction of a predefined amount and for a minimum time period. Response duration usually is measured from the time of initial response until documented tumor progression. Generally, the U.S. FDA has defined ORR as the sum of partial responses plus complete responses. When defined in this manner, ORR is a direct measure of drug antitumor activity, which can be evaluated in a single-arm study. Stable disease should not be a component of ORR. Stable disease can reflect the natural history of disease, whereas tumor reduction is a direct therapeutic effect. The significance of ORR is assessed by its magnitude and duration, and the percentage of complete responses (no detectable evidence of tumor).

As used herein, the term "time to progression" (TPP) refers to the time from randomization until objective tumor progression; TTP does not include deaths.

As used herein, the term "relapse-free survival" (RFS) refers to the length of time after primary treatment for a cancer ends that the patient survives without any signs or symptoms of that cancer. In a clinical trial, measuring the relapse-free survival is one way to see how well a new treatment works. The term is also interchangeable in the art as disease-free survival (DFS).

As used herein, the term "progression-free survival" (PFS) means the time from randomization in a clinical trial until progression or death.

As used herein, the term "event-free survival" (EFS) means the time from study entry until any treatment failure, including disease progression, treatment discontinuation for any reason, or death.

As used herein, the term "duration of response" (DoR) is the time from achieving a response until relapse or disease progression.

As used herein, the term "patient" refers to a mammal, including mice, rats, dogs and humans, which is afflicted with a brain tumor (e.g., a glioma). In some embodiments, the patient is a human.

In some embodiments, the compound of formula (I), or a pharmaceutically acceptable salt thereof, is administered in an amount of from 1 to 5000 mg/day, 50 to 2000 mg/day, 100 to 1000 mg/day, 250 to 750 mg/day, or 400 to 600 mg/day, or 500 mg/day (e.g., 500 mg QD or 250 mg Q12H). In some embodiments, the compound of formula (I), or a pharmaceutically acceptable salt thereof, is administered once per day or more than once per day (e.g., twice per day, three times per day, four times per day, etc.) to achieve administration of the foregoing amounts per day. In some embodiments, the compound of formula (I), or a pharmaceutically acceptable salt thereof, is administered once per day to achieve administration of the foregoing amounts per day. In some embodiments, the compound of formula (I), or a pharmaceutically acceptable salt thereof, is administered twice per day to achieve administration of the foregoing amounts per day. In some embodiments, the compound of formula (I), or a pharmaceutically acceptable salt thereof, is administered once per day in an amount of 1 to 5000 mg, 50 to 2000 mg, 100 to 1000 mg, 250 to 750 mg, 400 to 600 mg, 450 to 550 mg, 475 to 525 mg, 490 to 510 mg, or about 500 mg per administration. In still other embodiments, the compound of formula (I), or a pharmaceutically acceptable salt thereof, is administered twice per day in an amount of 1 to 2500 mg, 25 to 1000 mg, 50 to 500 mg, 125 to 375 mg, 200 to 300 mg, 225 to 275 mg, 245 to 255 mg, or about 250 mg per administration. In other embodiments, the compound of formula (I), or a pharmaceutically acceptable salt thereof, is administered in an amount of from 0.1 to 50 mg/kg of body weight per day, 1 to 25 mg/kg of body weight per day, 2 to 20 mg/kg of body weight per day, 3 to 15 mg/kg of body weight per day, 5 to 10 mg/kg of body weight per day, 3 to 7 mg/kg of body weight per day, or 8 to 12 mg/kg of body weight per day. The amounts of the compound of formula (I), or a pharmaceutically acceptable salt thereof, set forth herein are based on the amount of the compound of formula (I). Specific dosage and treatment regimens for any particular subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

In some embodiments, the radiation therapy is administered in a manner consistent with the National Comprehensive Cancer Network Clinical Practice Guidelines in Oncology (e.g., dose and schedule of administration), version 1.2016 available at nccn.org. In some embodiments, the radiation therapy is administered in a cumulative dose of 20-100 Gy, or 30-80 Gy, or 30-60 Gy, or 40-70 Gy, or 40-60 Gy, or 30-40 Gy, or 40-50 Gy, or 50-60 Gy, or 45-55 Gy, in 1.0-5.0 Gy fractions, or 1.5-3.0 Gy fractions, or 1.0-1.5 Gy fractions, or 1.5-2.0 Gy fractions, or 2.0-2.5 Gy fractions, or 2.5-3.0 Gy fractions, or 1.8-2.0 Gy fractions, or 1.8 Gy fractions, or 2.0 Gy fractions. In some embodiments, the radiation therapy is administered in a cumulative dose of 50-70 Gy in 1.5-2.5 Gy fractions, or 60 Gy in 2.0 Gy fractions. The cumulative dose refers to the total of all of the fractional doses given during a course of treatment.

The dose of radiation therapy may be selected based on the nature of the brain tumor. In some embodiments where the brain tumor is a low grade glioma, the radiation therapy is administered in a cumulative dose of 40-50 Gy in 1.5-2.5 Gy fractions, or in a cumulative dose of 45-54 Gy in 1.8-2.0 Gy fractions, or in a cumulative dose of 45.5 Gy in 1.8-2.0 Gy fractions. In some embodiments where the brain tumor is a high grade glioma, the radiation therapy is administered in a cumulative dose of 50-70 Gy in 1.5-2.5 Gy fractions, or in a cumulative dose of 59.4 Gy in 1.8 Gy fractions, or in a cumulative dose of 55.8-59.4 Gy in 1.8 Gy fractions, or in a cumulative dose of 57 Gy in 1.9 Gy fractions, or in a cumulative dose of 60 Gy in 1.8-2.0 Gy fractions, or 25 Gy in 5.0 Gy fractions. In some embodiments where the brain tumor is a glioblastoma, the radiation therapy is administered in a cumulative dose of 30-60 Gy in 2.0-4.0 Gy fractions, or in a cumulative dose of 34 Gy in 3.4 Gy fractions, or in a cumulative dose of 35-45 Gy in 2.5-3.0 Gy fractions, or in a cumulative dose of 50 Gy in 2.5 Gy fractions.

Additional Therapeutic Agents

As used here, the "one or more additional therapeutic agents" employed in the methods described herein include those agents that are known to be useful for treating brain tumors, i.e., having a therapeutic effect on, alleviating one or more symptoms of, altering the progression of, eradicating, reducing the size of, slowing or inhibiting the growth of, delaying or minimizing one or more symptoms associated with, reducing the malignancy of, or inducing stasis of the brain tumor, or alleviating or minimizing one or more side effects associated with another therapy applied or administered to treat the brain tumor.

In some embodiments, the one or more additional therapeutic agents include one or more of a DNA-reactive agent, a PARP inhibitor, an anti-emesis agent, an anti-convulsant or anti-epileptic agent, a checkpoint inhibitor, PVC chemotherapy, bevacizumab, and gemcitabine.

In some embodiments, the one or more additional therapeutic agents is a DNA-reactive agent. As used herein, "DNA-reactive agents" are those agents, such as alkylating agents, cross-linking agents, and DNA intercalating agents, which interact covalently or non-covalently with cellular DNA. For example, DNA-reactive agents include adozelesin, altretamine, bizelesin, busulfan, carboplatin, carboquone, carmustine, chlorambucil, cisplatin, cyclophosphamide, dacarbazine, estramustine, fotemustine, hepsulfam, ifosfamide, improsulfan, irofulven, lomustine, mechlorethamine, melphalan, mitozolomide, nedaplatin, oxaliplatin, piposulfan, procarbazine, semustine, streptozocin, temozolomide, thiotepa, treosulfan, diethylnitrosoamine, benzo(a)pyrene, doxorubicin, mitomycin-C, and the like. Many of these DNA-reactive agents are useful in cancer therapy as DNA-reactive chemotherapeutic agents.

In some embodiments, the DNA-reactive agent is temozolomide (TMZ). In one aspect of these embodiments, the TMZ is administered in a manner consistent with the National Comprehensive Cancer Network Clinical Practice Guidelines in Oncology (e.g., dose and schedule of administration), version 1.2016 available at nccn.org. In one aspect of these embodiments, the TMZ is administered in a manner consistent with the prescribing information for TEMODAR® (temozolomide) Capsules and TEMODAR® (temozolomide) for Injection. In some aspects of these embodiments, the TMZ is administered in a daily dose of 100-250 mg/m$^2$ based on the patient's body surface area, or 100-150 mg/m$^2$, or 150-200 mg/m$^2$, or 200-250 mg/m$^2$. In some aspects of these embodiments, the TMZ is administered in a daily dose of 50-100 mg/m$^2$ based on the patient's body surface area, or 50-75 mg/m$^2$, or 75-100 mg/m$^2$, or 60-90 mg/m$^2$, or 65-85 mg/m$^2$, or 70-80 mg/m$^2$. In some aspects of these embodiments, the TMZ is administered in a daily dose of 125-175 mg/m$^2$ based on the patient's body surface area for 5 consecutive days of a 28-day treatment cycle. In some aspects of these embodiments, the TMZ is administered in combination with radiation therapy in a daily dose of 50-100 mg/m$^2$ based on the patient's body surface area, or 50-75 mg/m$^2$, or 75-100 mg/m$^2$, or 60-90 mg/m$^2$, or 65-85 mg/m$^2$, or 70-80 mg/m$^2$. In some aspects of these embodiments, the TMZ is administered in combination with radiation therapy in a daily dose of 70-80 mg/m$^2$ based on the patient's body surface area for 42 days. In some aspects of these embodiments where the brain tumor is a high grade glioma or glioblastoma, the TMZ is administered in combination with radiation therapy in a daily dose of 70-80 mg/m$^2$ based on the patient's body surface area for 42 days. In some aspects of these embodiments where the brain tumor is an anaplastic astrocytoma, the TMZ is administered in a daily dose of 125-175 mg/m$^2$ based on the patient's body surface area for 5 consecutive days of a 28-day treatment cycle. In some aspects of these embodiments where the brain tumor is an anaplastic astrocytoma, the TMZ is administered in a daily dose of 175-225 mg/m$^2$ based on the patient's body surface area for 5 consecutive days of a 28-day treatment cycle.

In some embodiments, the one or more additional therapeutic agents is a PARP inhibitor. As used herein, "PARP inhibitor" refers to an inhibitor of the enzyme poly ADP ribose polymerase (PARP). Examples of PARP inhibitors include pamiparib, olaparib, rucaparib, velaparib, iniparib, talazoparib, niraparib, and the like.

In some embodiments, the one or more additional therapeutic agents is an anti-emesis agent. As used herein, "anti-emesis agent" refers to a drug that is effective to reduce vomiting and nausea symptoms. Examples of anti-emesis agents include 5-HT$_3$ receptor antagonists (e.g., dolasetron, granisetron, ondansetron, tropisetron, palonosetron, mirtazapine, and the like), dopamine agonists (e.g., domperidone, olanzapine, droperidol, haloperidol, chlorpromazine, prochlorperazine, alizapride, prochlorperazine, metoclopramide, and the like), NK1 receptor antagonists (e.g., aprepitant, casopitant, rolapitant, and the like), antihistamines (e.g., cinnarizine, cyclizine, diphenhydramine, dimenhydrinate, doxylamine, meclizine, promethazine, hydroxyzine, and the like), cannabinoids (e.g, cannabis, dronabinol, synthetic cannabinoids, and the like), benzodiazepines (e.g., midazolam, lorazepam, and the like), anticholinergics (e.g., scopolamine and the like), steroids (e.g., dexamethasone and the like), trimethobenzamide, ginger, propofol, glucose/fructose/phosphoric acid (which is sold under the trade name Emetrol®), peppermint, muscimol, ajwain, and the like.

In some embodiments, the one or more additional therapeutic agents is an anti-convulsant or anti-epileptic agent. As used herein, "anti-convulsant or anti-epileptic agent" refers to a drug that is effective for treating or preventing seizures, including epileptic seizures. Examples of anti-convulsants include paraldehyde, stiripentol, phenobarbital, methylphenobarbital, barbexaclone, clobazam, clonazepam, clorazepate, diazepam, midazolam, lorazepam, nitrazepam, temazepam, nimetazepam, potassium bromide, felbamate, carbamazepine, oxcarbazepine, eslicarbazepine acetate, valproic acid, sodium valproate, divalproex sodium, vigabatrin, progabide, tiagabine, topiramate, gabapentin, pregabalin, ethotoin, phenytoin, mephenytoin, fosphenytoin, paramethadione, trimethadione, ethadione, beclamide, primidone, brivaracetam, etiracetam, levetiracetam, seletracetam, ethosuximide, phensuximide, mesuximide, acetazolamide, sultiame, methazolamide, zonisamide, lamotrigine, pheneturide, phenacemide, valpromide, valnoctamide, perampanel, stiripentol, pyridoxine, and the like.

In some embodiments, the one or more additional therapeutic agents is a checkpoint inhibitor. As used herein, "checkpoint inhibitor" refers to a therapeutic agent that inhibits an immune checkpoint (e.g., CTLA-4, PD-1/PD-L1, and the like) that otherwise would prevent immune system attacks on cancer cells, thereby allowing the immune system to attack the cancer cells. Examples of check point inhibitors include ipilimumab, nivolumab, pembrolizumab, atezolizumab, avelumab, durvalumab, BGB-A317, spartalizumab, and the like.

In some embodiments, the one or more additional therapeutic agents is PVC chemotherapy. As used herein, "PVC chemotherapy" refers to a chemotherapy regimen comprising the combined administration of procarbazine, lomustine (which is sold under the trade name CCNU®), and vincristine (which is sold under the trade name Onocovin®). Typically, the vincristine is administered intravenously, while the procarbazine, and lomustine are administered orally. PCV chemotherapy often is administered in cycles, wherein each cycle comprises a single administration of vincristine and lomustine and a 10-day course of treatment with procarbazine.

In some embodiments, the one or more additional therapeutic agents is bevacizumab. Bevacizumab, which is sold under the trade name Avastin®, is a recombinant humanized monoclonal antibody.

In some embodiments, the one or more additional therapeutic agents is gemcitabine. Gemcitabine, which is sold under the trade name Gemzar®, is a pyrimidine nucleoside analog.

Brain Tumors Treated by Methods of the Invention

The methods of the invention are useful for treating brain tumors. This includes all tumors inside the human skull (cranium) or in the central spinal canal. The tumor may originate from the brain itself, but also from lymphatic tissue, blood vessels, the cranial nerves, the brain envelopes (meninges), skull, pituitary gland, or pineal gland. Within the brain itself, the involved cells may be neurons or glial cells (which include astrocytes, oligodendrocytes, and ependymal cells). Brain tumors may also spread from cancers primarily located in other organs (metastatic tumors).

In some embodiments, the brain tumor is a glioma, such as an ependymoma, astrocytoma, oligoastrocytoma, oligodendroglioma, ganglioglioma, glioblastoma (also known as glioblastoma multiforme), or mixed glioma. Gliomas are primary brain tumors and are classified into four grades (I, II, III, and IV) based on their appearance under a microscope, and particularly the presence of atypical cells, mitoses, endothelial proliferation, and necrosis. Grade I and II tumors, termed "low-grade gliomas," have none or one of these features and include diffuse astrocytomas, pilocytic astrocytomas, low-grade astrocytomas, low-grade oligoastrocytomas, low-grade oligodendrogliomas, gangliogliomas, dysembryoplastic neuroepithelial tumors, pleomorphic xanthoastrocytomas, and mixed gliomas. Grade III and IV tumors, termed "high-grade gliomas," have two or more of these features and include anaplastic astrocytomas, anaplastic oligodendrogliomas, anaplastic oligoastrocytomas, anaplastic ependymomas, and glioblastomas (including giant cell glioblastomas and gliosarcomas). In one aspect of these embodiments, the glioma is a low grade glioma. In another aspect of these embodiments, the glioma is a high grade glioma. In another aspect of these embodiments, the glioma is a glioblastoma.

In some embodiments, the brain tumor (e.g., glioma) to be treated is characterized by the presence of an IDH1 mutation, wherein the IDH1 mutation results in accumulation of R(−)-2-hydroxyglutarate in a patient. In one aspect of these embodiments, the IDH1 mutation results in accumulation of R(−)-2-hydroxyglutarate in a patient by providing a new ability of the enzyme to catalyze the NADPH-dependent reduction of α-ketoglutarate to R(−)-2-hydroxyglutarate in a patient. In another aspect of these embodiments, the IDH1 mutation is an R132X mutation. In another aspect of these embodiments, the R132X mutation is selected from R132H, R132C, R132L, R132V, R132S and R132G. In another aspect of these embodiments, the R132X mutation is R132H or R132C. In yet another aspect of these embodiments, the R132X mutation is R132H. In still another aspect of these embodiments, at least 30, 40, 50, 60, 70, 80 or 90% of the brain tumor (e.g., glioma) cells carry an IDH1 R132X mutation, such as an R132H, R132C, R132L, R132V, R132S or R132G mutation, at the time of diagnosis or treatment. A brain tumor (e.g., glioma) can be analyzed by sequencing cell samples to determine the presence and specific nature of (e.g., the changed amino acid present at) a mutation at amino acid 132 of IDH1.

In still other embodiments, the brain tumor (e.g., glioma) to be treated is characterized by the presence of an IDH1 allele that does not include an R132X mutation. In one aspect of these embodiments, at least 90% of the brain tumor (e.g., glioma) cells do not include a mutation at amino acid 132 of IDH1. A brain tumor (e.g., glioma) can be analyzed by sequencing cell samples to determine the presence or absence of a mutation at amino acid 132 of IDH1.

Compound and Pharmaceutically Acceptable Salts Thereof Used in Methods of the Invention The compound of formula (I) used in the methods described herein is known as (S)—N—((S)-1-(2-Chlorophenyl)-2-(3,3-difluorocyclobutylamino)-2-oxoethyl)-1-(4-cyanopyridin-2-yl)-N-(5-fluoropyridin-3-yl)-5-oxopyrrolidine-2-carboxamide and is referred to in the Example as ivosidenib.

The compound of formula (I) can be prepared by the method described in paragraphs [0301]-[0308], and [0369]-[0372] of U.S. Publication No. 2013/0190249 A1, which paragraphs are incorporated herein by reference.

As used herein, the terms "compound" and "pharmaceutically acceptable salt," when referring to the compound of formula (I) and pharmaceutically acceptable salts thereof, include the specified compound and pharmaceutically acceptable salts in any form, including any tautomer or rotamer thereof, any solid form thereof (including any polymorphic form thereof), any solvate or hydrate form thereof, any cocrystal thereof, and any solution thereof.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" of the compound of formula (I) includes any non-toxic salt that, upon administration to a recipient, is capable of providing, either directly or indirectly, the compound of formula (I). Pharmaceutically acceptable salts are described in detail in S. M. Berge, et al., *J. Pharmaceutical Sciences*, 1977, 66, 1-19, incorporated herein by reference.

As used herein, the term "cocrystal" refers to a crystalline solid made up of two or more neutral chemical species in a defined stoichiometric ratio that possesses distinct crystallographic and spectroscopic properties when compared to the species individually. A "cocrystal" is distinct from a "salt," which is made up of charged-balanced charged species. The species making up a cocrystal typically are linked by hydrogen bonding and other non-covalent and non-ionic interactions. Thus, a pharmaceutical cocrystal of a drug typically comprises the drug and one or more coformers.

In the specification and claims, each atom of the compound of formula (I) is meant to represent any stable isotope of the specified element. In the Examples, no effort was made to enrich any atom of Compound A in a particular isotope, and therefore each atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

In some embodiments, the compound of formula (I), or a pharmaceutically acceptable salt thereof, includes each constituent atom at approximately the natural abundance isotopic composition of the specified element.

Compositions and Routes of Administration of the Compound of Formula (I), or a Pharmaceutically Acceptable Salt Thereof The compound of formula (I), or a pharmaceutically acceptable salt thereof, may be formulated together with a pharmaceutically acceptable carrier, adjuvant, or vehicle into pharmaceutical compositions prior to being administered to a subject.

The term "pharmaceutically acceptable carrier, adjuvant, or vehicle" refers to a carrier, adjuvant, or vehicle that may be administered to a subject, together with the compound of formula (I), or a pharmaceutically acceptable salt thereof, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of the compound of formula (I), or a pharmaceutically acceptable salt thereof.

The pharmaceutical compositions may be administered orally, parenterally, by inhalation spray, topically, rectally, nasally, buccally, vaginally or via an implanted reservoir, preferably by oral administration or administration by injection. The pharmaceutical compositions may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions may also be administered in the form of suppositories for rectal administration. These compositions can be prepared by mixing the compound of formula (I), or a pharmaceutically acceptable salt thereof, with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions may be administered topically to the skin. The pharmaceutical composition should be formulated with a suitable ointment containing the active components suspended or dissolved in a carrier. Carriers for topical administration of the compounds of one aspect of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of one aspect of this invention may also be topically applied to the lower intestinal tract by rectal suppository formulation or in a suitable enema formulation. Topically-transdermal patches are also included in one aspect of this invention.

The pharmaceutical compositions may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The amount of active ingredient that may be combined with the carrier materials to produce a single dosage form will vary depending upon the patient treated and the particular mode of administration. A typical preparation will contain from about 5% to about 95% active compound (w/w). Alternatively, such preparations contain from about 20% to about 80% active compound.

The pharmaceutical compositions comprising the compound of formula (I), or a pharmaceutically acceptable salt thereof, may further comprise another therapeutic agent useful for treating cancer, such as a DNA-reactive agent (defined above).

The pharmaceutical compositions comprising the compound of formula (I), or a pharmaceutically acceptable salt thereof, may further comprise one or more additional therapeutic agents (e.g., DNA-reactive agent).

Routes of Administration of Radiation Therapy

Radiation therapy involves the use of high-energy radiation (e.g., x-rays, gamma rays, or charged particles) to damage and/or kill cancer cells and to shrink tumors. In the methods of the invention, radiation may be delivered to the brain tumor (e.g., glioma) by a machine positioned outside the body (external-beam radiation therapy), by radioactive material placed in the body near the brain tumor (internal radiation therapy, also called brachytherapy), or by radioactive substances administered systemically (e.g., radioactive iodine) that travel through the bloodstream to the brain tumor. Alternatively, these delivery methods can be used in combination.

In some embodiments, the radiation therapy comprises external radiation therapy (e.g., external-beam radiation therapy including fractionated external-beam radiation therapy, stereotactic radiation such as Cyberknife® or Gamma Knife®, proton therapy, and the like), where the radiation is delivered to the brain tumor (e.g., glioma) by an instrument outside the body. External radiation therapy may be given as a course of several treatments over days or weeks. In one aspect of these embodiments, the radiation is administered in the form of x-rays.

In other embodiments, the radiation therapy comprises internal radiation therapy, where the radiation comes from an implant or a material (liquid, solid, semi-solid or other substance) placed inside the body. In one aspect of these embodiments, the internal radiation therapy is brachytherapy, where a solid radioactive source is placed inside the body near the brain tumor. In another aspect of these embodiments, the internal radiation therapy comprises the systemic administration of a radiation source, typically a radionuclide (radioisotope or unsealed source). The radiation source may be orally administered or may be injected into a vein.

Additional Treatments and Therapeutic Agents

In some embodiments, the methods described herein further comprise the additional step of administering to the patient an additional cancer therapeutic agent or an additional cancer treatment.

For example, the methods described herein may be practiced in combination with the existing standard of care therapy for glioma. The standard of care for patients diagnosed with glioma considers the tumor location, potential symptoms, and potential benefits versus risks of the different treatment options (modalities). Upon initial diagnosis of glioma, standard treatment consists of maximal surgical resection, radiotherapy, and/or concomitant and adjuvant chemotherapy (e.g. with temozolomide (TMZ)). For patients older than 70 years, less aggressive therapy is sometimes employed, using radiation TMZ alone. (See generally National Comprehensive Cancer Network Guidelines, version 1.2016 available at nccn.org.)

For example, the current regimen for treatment of primary grade IV glioblastoma (GBM) is surgical resection in combination with radiation therapy and chemotherapy. Current U.S. FDA approved chemotherapies for primary grade IV GBM tumors include nitrosoureas (lomustine and carmustine) and TMZ. Glioma post-surgical standard of care therapy consists of radiation and TMZ as antineoplastic therapy and dexamethasone (DEX) for neurological symptomatic relief. More recently, the antibody to vascular endothelial growth factor (VEGF), bevacizumab, is being used more often for tumor recurrence. Numerous experimental agents are in various phases of pre-clinical and clinical application are in development and may result in changes to the standard of care for glioblastoma.

The methods described herein can be combined with radiation therapy or surgery. In certain embodiments, the methods are practiced on a patient who is undergoing radiation therapy, has previously undergone radiation therapy or will be undergoing radiation therapy. In certain embodiments, the methods are practiced on a patient who has undergone brain tumor removal surgery. Further provided herein are methods for treating patients who have been previously treated for a brain tumor, but are non-responsive to standard therapies, for example with Temozolomide, as well as those who have not previously been treated. Further provided herein are methods for treating patients who have undergone surgery in an attempt to treat the condition at issue, as well as those who have not. Because patients with brain tumors may have heterogeneous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with a brain tumor. In some embodiments, the methods described herein additionally comprise administration of Temozolomide. In some such embodiments, the brain tumor is Temozolomide resistant.

Exemplary additional cancer therapeutic agents include for example, chemotherapy, targeted therapy, immunotherapy, anti-epileptics, steroids, checkpoint inhibitors, CAR-Ts, Gliadel® (carmustine implant), and Avastin® (bevacizumab). Additional cancer treatments include, for example: surgery, and radiation therapy.

In some embodiments the additional cancer therapeutic agent is a targeted therapy agent. Targeted therapy constitutes the use of agents specific for the deregulated proteins of cancer cells. Small molecule targeted therapy drugs are generally inhibitors of enzymatic domains on mutated, overexpressed, or otherwise critical proteins within the cancer cell. Prominent examples are the tyrosine kinase inhibitors such as Axitinib, Bosutinib, Cediranib, dasatinib, erlotinib, imatinib, gefitinib, lapatinib, Lestaurtinib, Nilotinib, Semaxanib, Sorafenib, Sunitinib, and Vandetanib, and also cyclin-dependent kinase inhibitors such as Alvocidib and Seliciclib. In some embodiments, the targeted therapy can be used in combination with the methods described herein, e.g., a biguanide such as metformin or phenformin, preferably phenformin.

Targeted therapy can also involve small peptides as "homing devices" which can bind to cell surface receptors or affected extracellular matrix surrounding the tumor. Radionuclides which are attached to these peptides (e.g., RGDs) eventually kill the cancer cell if the nuclide decays in the vicinity of the cell. An example of such therapy includes BEXXAR®.

In some embodiments, the additional cancer therapeutic agent is an immunotherapy agent. Cancer immunotherapy refers to a diverse set of therapeutic strategies designed to induce the subject's own immune system to fight the tumor.

Allogeneic hematopoietic stem cell transplantation can be considered a form of immunotherapy, since the donor's immune cells will often attack the tumor in a graft-versus-tumor effect. In some embodiments, the immunotherapy agents can be used in combination with the methods described herein.

Other possible additional therapeutic modalities include imatinib, gene therapy, peptide and dendritic cell vaccines, synthetic chlorotoxins, and radiolabeled drugs and antibodies.

EXAMPLES

Abbreviations

Unless otherwise noted, or where the context dictates otherwise, the following abbreviations shall be understood to have the following meanings:

| Abbreviation | Meaning |
| --- | --- |
| IDH1 | Isocitrate Dehydrogenase 1 |
| IDH1m | Mutant Isocitrate Dehydrogenase 1 |
| R132H | Arginine to histidine point mutation at codon 132 of IDH1 |
| IDH1$^{R132H}$ | IDH1 having an R132H point mutation |
| EGF | Epidermal growth factor |
| bFGF | Basic fibroblast growth factor |
| MRI | Magnetic resonance imaging |
| 2HG | 2-hydroxyglutarate |
| PO | Per Os (oral administration) |
| SARRP | Small Animal Radiation Research Platform |
| QD | Quaque Die (administration once per day) |
| QDxN | Quaque Die (administration once per day) for N days |
| Q12H | Administration every 12 hours |
| Q12Hx2 | Administration every 12 hours for 2 administrations |
| (Q12Hx2) | Administration every 12 hours for 2 administrations per |
| QDx17 | day for 17 days (34 total administrations), could also be written as "Q12Hx34" or "every 12 hours for 17 days" |
| (Q12Hx2) | Administration every 12 hours for 2 administrations per |
| QDxN | day for N days |
| BID | Bis in Die (administration twice per day) |
| T2w | T2-weighted |
| rcf | Relative centrifugal force |
| TMZ | Temozolomide |
| Gy | Gray |
| RT | Radiation therapy |
| BED | Biological effective dose |
| mm | Millimeters |
| mg | Milligrams |
| ng | Nanograms |
| kg | kilograms |
| mL | Milliliters |
| min | Minutes |
| MAD | Median absolute distribution |
| SEM | Standard error of the mean |
| HPMCAS | Hypromellose acetate succinate |

Example 1

Combination of Ivosidenib and Radiation Therapy in IDH1m Glioma Model

Study Objective:

The objective of this study was to evaluate the potential efficacy of ivosidenib, given twice daily, alone and in combination with focal beam radiation, against established orthotopic human neurosphere-derived grade III glioma cells carrying an IDH1 R132H mutation in female mice using magnetic resonance imaging (MRI).

Study Design:

The study mice were imaged by MRI on Days 37 and 38 post inoculation and sorted into five study groups based on MRI estimation of tumor burden. Staging values are recorded on Day 38. Treatment began on Day 37 post inoculation with the treatment schedules summarized in Table 1.

TABLE 1

Study Design/Treatment Schedules

| Group | # of Animals | Treatment | Route | Dose and Schedule |
|---|---|---|---|---|
| 1 | 10 | Vehicle Control (1.5% HPMCAS/0.5% methylcellulose/ 0.2% Tween80 in water) | PO | Protocol: 0.2 mL/20 g, (Q12Hx2) QDx17 Actual: 0.2 mL/20 g, (Q12x2) QDx25 (Days 37-61)* |
| 2 | 10 | Focal Radiation (SARRP) | SARRP | Protocol: 2 Gy, QDx5 Actual: 2 Gy, QDx5 (Days 37-41) |
| 3 | 10 | Ivosidenib | PO | Protocol: 150 mg/kg, (Q12Hx2) QDx17 Actual: 150 mg/kg, (Q12Hx2) QDx25 (Days 37-61)* |
| 4 | 10 | Ivosidenib + Focal Radiation (SARRP) (simultaneous treatment) | PO + SARRP | Protocol: Ivosidenib: 150 mg/kg, (Q12Hx2) QDx17 Focal Radiation: 2 Gy, QDx5 Actual: Ivosidenib: 150 mg/kg, (Q12Hx2) QDx32 (Days 37-68)* Focal Radiation: 2 Gy, QDx5 (Days 37-41) |
| 5 | 10 | Focal Radiation (SARRP), then Ivosidenib (sequential treatment, with Ivosidenib administration beginning 24 hours after last radiation session) | SARRP, then PO | Protocol: Focal Radiation: 2 Gy, QDx5 Ivosidenib: 150 mg/kg, (Q12Hx2) QDx17 Actual: Focal Radiation: 2 Gy, QDx5 (Days 37-41) Ivosidenib: 150 mg/kg, (Q12Hx2) QDx27 (Days 42-68)* |

Protocol deviations reflected in Table 1 were as follows:
* For Groups 1, 3, 4, and 5, administration of Ivosidenib or the Vehicle Control was extended until study termination. The dosing schedule specified in Table 1 ((Q12Hx2) QDx17) was the planned dosing schedule for each Group. However, for each Group, dosing was continued until no animals were left in that Group. Dosing was continued for the duration of the time period specified for each Group in Table 1. Extensions of dosing are common in in vivo studies. In the case of this study, tumor volumes were still within a range that allowed mice to receive treatment with either vehicle or Ivosidenib beyond that which was predicted ahead of study.

The foregoing protocol deviations are not believed to have affected the results of the study.

Materials and Methods:

The study animals (female mice obtained from Envigo) were implanted intracranially on Day 0 of the study with $5 \times 10^4$ cells bearing the $IDH1^{R132H}$ mutation. The cell line is a primary derived human glioma cell line generated by the Mellinghoff lab (Memorial Sloan Kettering Cancer Institute/ NYC) and is identified as the TS603 cell line. The cell line was cultured in StemCell Technologies NeuroCult media, with Neurocult NS supplement, 0.0002% Heparin, 20 ng/mL EGF, and 10 ng/mL bFGF. All mice were imaged by magnetic resonance imaging (MRI) on Days 35 and 36 and sorted into study groups based on MRI estimation of tumor burden, and the staging values were recorded as Day 36. Treatment began on Day 37 with the dosing schedules set forth in Table 1.

Ivosidenib was prepared to meet dose level requirements. The compound was formulated at a concentration of 5 mg/mL in a vehicle of 0.5% methylcellulose, 0.2% Tween 80, and water. The formulation was prepared fresh daily, and was stirred for at least one hour prior to dosing. The dosing formulation was stored at 4° C. between doses.

Ivosidenib was orally dosed at 150 mg/kg, twice daily, for Groups 3-5. The dose of ivosidenib was chosen based on historical data that at this dose, which showed that 2HG production is inhibited at >98% within the brain tumors, when compared to healthy brain tissue.

Radiation treatment was administered via the Xstrahl Life Sciences Small Animal Radiation Research Platform, or SARRP. This system has been designed to allow for highly targeted irradiation which mimics that applied in human patients. The x-ray tube on the SARRP has variable output and is used for Computed Tomography (CT) imaging to guide treatment and also for treatment delivery with single or multiple beams. The total amount of radiation delivered to the tumor was 10 Gy/mouse (2 Gy, QDx5) for Groups 2, 4, and 5.

Group 1 was anesthetized on the same treatment schedule.

T2-weighted (T2w) magnetic resonance images (MRI) were acquired such that volumetric measurements could be assessed to determine disease progression. In vivo magnetic resonance imaging was performed using a Bruker 7T MRI system. T2-weighted anatomical magnetic resonance scans were conducted on Days 36, 40, 44, 48, 51, 56, 58, 62, and 65.

Results:

Treatment with the vehicle was well tolerated, resulting in no treatment-related mortality. Treatment was associated with a 32.7% body weight loss, most of which appeared to be due to advancing tumor burden and not vehicle or anesthesia. Mice began to show clinical signs on Day 40. The majority of the mice in the group began to develop rough pelage, hunched posture, and dehydration beginning on Days 47 and 49.

Treatment with radiation therapy alone (Group 2), Ivosidenib alone (Group 3), concurrent administration of Ivosidenib and radiation therapy (Group 4), and sequential administration of radiation therapy followed by Ivosidenib (Group 5) were compared. Tumor volume estimates from MRI found that, of the mice receiving the combined therapies, Group 4 demonstrated no significantly different tumor burden as compared to radiation therapy alone (Group 2), while Group 5 did show a significantly reduced tumor burden as compared to radiation therapy alone (Group 2), when each group was compared to vehicle treated mice (Group 1). The median measured tumor volumes (in $mm^3$) of the animals in each Group up to and including Day 58 are reported in Table 2 and FIG. 1. The tumor volumes measured on Days 62 and 65 are not included in FIG. 1 because Group 1 was terminated after Day 61 and therefore, comparison to the Vehicle Control is not possible for later time points. The error bars in FIG. 1 correspond to the median absolute distribution for each data point.

TABLE 2

Measured Tumor Volumes

| Day (post inoculation) | Group 1 Median (MAD) | Group 2 Median (MAD) | Group 3 Median (MAD) | Group 4 Median (MAD) | Group 5 Median (MAD) |
|---|---|---|---|---|---|
| 38 | 7.45 (2.3) | 7.65 (2.3) | 7.4 (2.2) | 7.4 (2.1) | 7.4 (2.1) |
| 40 | 23.2 (6.2) | 22.55 (6.5) | 16.75 (5.9) | 23.8 (9.2) | 19.55 (4.9) |
| 44 | 49.8 (11.55) | 34.9 (13.15) | 58.15 (16.4) | 46.2 (10.4) | 35.85 (8.3) |
| 48 | 89.7 (28) | 72.7 (10.1) | 111.35 (26.5) | 60.45 (15.25) | 65.7 (22.8) |
| 51 | 127.75 (19.85) | 78.2 (15.7) | 142.5 (15.5) | 63 (16.2) | 61.4 (15.3) |
| 56 | 178.9 (26.7) | 70.8 (14.05) | 147.8 (15.5) | 61.7 (16.15) | 61.65 (12.85) |
| 58 | 187.25 (20.85) | 70.3 (11.55) | 154.2 (18.3) | 59.75 (7.65) | 53.05 (11.25) |

As shown in Table 3, the differences in tumor burden on Day 58 between the specified groups were statistically significant. Data points were carried through the study to be able to incorporate tumor volumes from all mice as they exited at different stages of the study due to disease burden. Statistical significance of the final data was carried out using an unpaired, Mann-Whitney test between groups.

TABLE 3

Statistical Analysis of Median Tumor Volumes

| Comparison | P-Value |
|---|---|
| Group 2 versus Group 1 | <0.0001 |
| Group 4 versus Group 1 | <0.0001 |
| Group 5 versus Group 1 | <0.0001 |
| Group 5 versus Group 2 | 0.024 |

Thus, while it had been suggested from in vitro experiments that administration of an mIDH1 inhibitor during radiation therapy desensitizes mIDH1 cells to the radiation therapy (R. J. Molenaar et al., Cancer Research 75:4790-4802 (2015)), the results shown in FIG. 1 demonstrate that the combination of Ivosidenib and radiation therapy shows no antagonism in vivo in an orthotopic mutant IDH1 glioma brain tumor model.

Example 2

Combination of Ivosidenib and Radiation Therapy in IDH1m Glioma

Study Objective:

The objective of this study was to evaluate the potential efficacy of Ivosidenib, given twice daily, alone and in combination with focal beam radiation, against established orthotopic human neurosphere-derived grade III glioma cells carrying an IDH1 R132H mutation in female mice using survival as the end point.

Study Design:

The study mice were imaged by MRI on Days 37 and 38 post inoculation and sorted into five study groups based on MRI estimation of tumor burden. Staging values were recorded on Day 38. Treatment began on Day 40 post inoculation with the treatment schedules summarized in Table 4.

TABLE 4

Study Design/Treatment Schedules

| Group | # of Animals | Treatment | Route | Dose and Schedule |
|---|---|---|---|---|
| 1 | 12 | Vehicle Control (1.5% HPMCAS/ 0.5% methylcellulose/ 0.2% Tween80 in water) | PO | Protocol: 0.2 mL/20 g, (Q12Hx2) QDx17 Actual: 0.2 mL/20 g, (Q12Hx2) QDx29 (Days 39-67)* |
| 2 | 12 | Focal Radiation (SARRP) | SARRP | Protocol: 2 Gy, 10 mm Collimator, QDx5 Actual: 2 Gy, 10 mm Collimator, QDx5** (Days 40-44) |

TABLE 4-continued

Study Design/Treatment Schedules

| Group | # of Animals | Treatment | Route | Dose and Schedule |
|---|---|---|---|---|
| 3 | 12 | Ivosidenib | PO | Protocol:<br>150 mg/kg, (Q12Hx2) QDx17<br>Actual:<br>150 mg/kg, (Q12Hx2) QDx25<br>(Days 39-63)* |
| 4 | 12 | Ivosidenib + Focal Radiation (SARRP) (simultaneous treatment) | PO + SARRP | Protocol:<br>Ivosidenib: 150 mg/kg, (Q12Hx2) QDx17<br>Focal Radiation: 2 Gy, 10 mm Collimator, QDx5<br>Actual:<br>Ivosidenib: 150 mg/kg, (Q12Hx2) QDx53<br>(Days 39-91)*<br>Focal Radiation: 2 Gy, 10 mm Collimator, QDx5**<br>(Days 40-44) |
| 5 | 12 | Focal Radiation (SARRP), then Ivosidenib (sequential treatment, with Ivosidenib administration beginning 24 hours after last radiation session) | SARRP, then PO | Protocol:<br>Focal Radiation: 2 Gy, 10 mm Collimator, QDx5<br>Ivosidenib: 150 mg/kg, (Q12Hx2) QDx17<br>Actual:<br>Focal Radiation: 2 Gy, 10 mm Collimator, QDx5**<br>(Days 40-44)<br>Ivosidenib: 150 mg/kg, (Q12Hx2) QDx44<br>(Days 45-88)* |

Protocol deviations reflected in Table 4 were as follows:

* For Groups 1, 3, 4, and 5, administration of Ivosidenib was extended until study termination. The dosing schedule specified in Table 4 ((Q12x2) QDx17) was the planned dosing schedule for each Group. However, for each Group, dosing was continued until no animals were left in that Group. Dosing was continued for the duration of the time period specified for each Group in Table 4. Extensions of dosing are common in in vivo studies. In the case of this study, tumor volumes were still within a range that allowed mice to receive treatment with either vehicle or Ivosidenib beyond that which was predicted ahead of study.

**An inadvertent error was made in the radiation treatment delivered in the first 2 days. This change shifted the treatment field off the brain, leading to the delivery of very little, if any, dose to the brain and tumor or the animal as a whole. To correct for this error, animals were given a dose of radiation at 2.6 Gy per day for 3 more days. This plan accelerated the delivery of the remaining 8 Gy by one day. No unexpected abrogation of tumor growth was observed; no unexpected weight loss was observed. The total amount of radiation delivered to the tumor was 10 Gy/mouse for Groups 2, 4, and 5.

The foregoing protocol deviations are not believed to have affected the results of the study.

Materials and Methods:

The study animals (female mice obtained from Envigo) were implanted intracranially on Day 0 of the study with $5\times10^4$ cells bearing the IDH1$^{R132H}$ mutation. The cell line was a primary derived human glioma cell line generated by the Mellinghoff lab (Memorial Sloan Kettering Cancer Institute/NYC) and was identified as the TS603 cell line. The cell line was cultured in StemCell Technologies NeuroCult media, with Neurocult NS supplement, 0.0002% Heparin, 20 ng/mL EGF, and 10 ng/mL bFGF.

T2-weighted (T2w) magnetic resonance images (MRI) were acquired such that volumetric measurements could be assessed to determine disease progression.

All mice were imaged by magnetic resonance on Days 37 and 38 and were sorted into study groups based on magnetic resonance estimation of tumor volume. The staging values were recorded as Day 38. All mice had a tumor burdens ranging from 5-20 mm$^3$. The mice were distributed to ensure that the mean tumor burden for all groups was within 10% of the overall mean tumor burden for the study population. Treatment began on Day 39.

Hydrogel® supplementation was added to all cages for all study mice on day 42, and was replenished daily until study termination. Subcutaneous fluids (lactated ringers) were given to all mice beginning on Day 41. Mice with less than 20% body weight loss received a total of 1.5 mL daily, while mice with more than 20% body weight loss received at total of 2 mL daily. Subcutaneous fluids for all mice were continued until study termination.

Ivosidenib was prepared to meet dose level requirements. The compound was formulated in a vehicle of 0.5% methylcellulose, 0.2% Tween80, and water. The formulation was prepared fresh daily, and was stirred for at least one hour prior to dosing. The dosing formulation was stored at 4° C. between dosing.

Ivosidenib was orally dosed at 150 mg/kg, twice daily, for Groups 3-5. The dose of ivosidenib was chosen based on historical data that at this dose, which showed that 2HG production is inhibited at >98% within the brain tumors, when compared to healthy brain tissue.

Radiation treatment was administered via the Xstrahl Life Sciences Small Animal Radiation Research Platform, or SARRP. This system has been designed to allow for highly targeted irradiation which mimics that applied in human patients. The x-ray tube on the SARRP has variable output and is used for Computed Tomography (CT) imaging to guide treatment and also for treatment delivery with single or multiple beams. The total amount of radiation delivered to the tumor was 10 Gy/mouse (2 Gy, QDx5) for Groups 2, 4, and 5.

Group 1 was anesthetized on the same treatment schedule.

At 6 hours after the morning dose of Ivosidenib, mice that exceeded euthanasia criteria (weight loss in excess of 30%, distended cranium, severely impaired movement, severe respiratory distress, and/or loss of righting reflex) were euthanized via overexposure to carbon dioxide for blood and brain collection.

Measurement and Endpoints:

The primary endpoint used for efficacy was increased lifespan.

Assessment of Side Effects. All animals were observed for clinical signs at least once daily. Animals were weighed on each day of treatment. Individual body weights were recorded 3 times weekly. Animals were euthanized for any one or a combination of the following events: weight loss in excess of 30%, distended cranium, severely impaired movement, severe respiratory distress, and/or loss of righting reflex.

Treatment related body weight loss and net treatment related body weight loss were also determined. Net weight loss was calculated by subtracting the vehicle control mean treatment related weight change from the weight change for each treated animal for that respective day. Treatment related body weight was monitored only in accordance with Institutional Animal Care and use Committee (IACUC) approved protocol measures. Treatment related body weight loss was concomitant with disease burden progression and unrelated to treatments on study.

Median Lifespan. The lifespan of each animal was measured from the day of first treatment (not the day of tumor implant) for each animal (Kaplan-Meier Survival—Log-Rank) and was used to calculate the median lifespan for each group. The calculation was based on the day of death for all animals that either died or were euthanized for disease or treatment related causes. Animals euthanized for sampling or therapy unrelated causes were excluded from this calculation.

The median lifespan for each group was used to calculate the % increase in lifespan (% ILS). % ILS is a group endpoint. It was calculated as follows:

% ILS={[(median treated lifespan)−(median control lifespan)]/(median control lifespan)}*100

P values and statistical significance for a comparison of the treatment groups (Groups 2-5) to the control group (Group 1) were determined using SigmaPlot 12.5 software.

Results:

The mean estimated tumor burden for all groups in the experiment on Day 38 was 9.5 mm$^3$, and all of the groups in the experiment were well-matched (range of group means, 9.4-9.6 mm$^3$). All animals weighed at least 14.7 g at the initiation of therapy. Mean group body weights at first treatment were also well-matched (range of group means, 18.5-20.1 g). The median control lifespan (Group 1) was 21 days.

The median lifespans and % ILS of Groups 2-5 are reported in Table 5.

TABLE 5

Median Lifespans and Percent Increases in Lifespan

| Group | Treatment | Median Lifespan | % ILS | P-Value (versus Control) |
|---|---|---|---|---|
| 1 | Control | 21 days | N/A | N/A |
| 2 | Focal Radiation | 45 days | 114% | <0.05 |
| 3 | Ivosidenib | 21 days | 0% | N/A |
| 4 | Ivosidenib + Focal Radiation (simultaneous treatment) | 45 days | 114% | <0.05 |
| 5 | Focal Radiation, then Ivosidenib (sequential treatment) | 42 days | 100% | <0.05 |

As shown in Table 5, the treatment groups receiving Focal Radiation (Group 2) and combination therapy involving Ivosidenib and Focal Radiation (Groups 4 and 5) experienced substantial increases in lifespan. The treatment groups receiving combination therapy (Groups 4 and 5) experienced comparable increases in lifespan to the group receiving Focal Radiation (Group 2).

Thus, while it had been suggested from in vitro experiments that administration of an mIDH1 inhibitor during radiation therapy desensitizes mIDH1 cells to the radiation therapy (R. J. Molenaar et al., Cancer Research 75:4790-4802 (2015)), the results shown in Table 8 demonstrate that the combination of Ivosidenib and radiation therapy shows no antagonism in vivo in an orthotopic mutant IDH1 glioma brain tumor model.

What is claimed is:

1. A method for treating glioma characterized by the presence of an IDH1 mutation in a patient in need thereof, comprising administering to the patient:
   (a) a daily dosage of from about 250 mg to about 750 mg of a compound of formula (I)

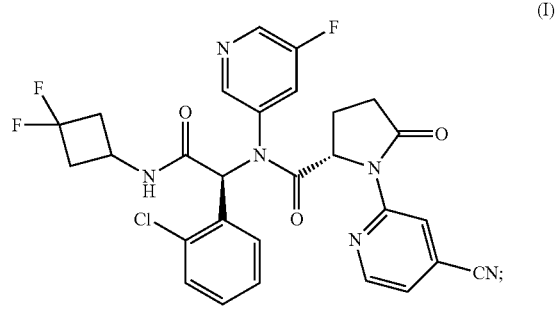 [SMILES: N#Cc1ccnc(N2C(=O)CC[C@H]2C(=O)N(c2cncc(F)c2)[C@H](C(=O)NC2CC(F)(F)C2)c2ccccc2Cl)c1]

or a pharmaceutically acceptable salt thereof; and
   (b) a cumulative daily dosage of from about 20 Gy to about 100 Gy of radiation therapy.

2. The method of claim 1, wherein said compound of formula (I), or a pharmaceutically acceptable salt thereof, and radiation therapy are administered concurrently.

3. The method of claim 1, wherein said compound of formula (I), or a pharmaceutically acceptable salt thereof, and radiation therapy are administered sequentially.

4. The method of claim 1, wherein said compound of formula (I), or a pharmaceutically acceptable salt thereof, is administered in an amount of from 400 to 600 mg/day.

5. The method of claim 1, wherein said compound of formula (I), or a pharmaceutically acceptable salt thereof, is administered once per day in an amount of about 500 mg per administration.

6. The method of claim 1, wherein said compound of formula (I), or a pharmaceutically acceptable salt thereof, is administered twice per day in an amount of about 250 mg per administration.

7. The method of claim 1, wherein said compound of formula (I) is administered in non-salt form.

8. The method of claim 1, wherein said radiation therapy is administered in the form of x-ray radiation.

9. The method of claim 1, wherein said radiation therapy is administered in a cumulative dose of from 30 to 60 Gy.

10. The method of claim 1, wherein the IDH1 mutation results in accumulation of R(−)-2-hydroxyglutarate in a patient.

11. The method of claim 1, wherein the IDH1 mutation is an R132X mutation.

12. The method of claim 1, wherein the IDH1 mutation is an R132H or R132C mutation.

13. The method of claim 1, wherein said radiation therapy comprises one or more of external-beam radiation therapy, brachytherapy, and systemic administration of a radiation source.

* * * * *